United States Patent
Yamamoto et al.

(10) Patent No.: US 9,889,155 B2
(45) Date of Patent: Feb. 13, 2018

(54) ENHANCER OF ANTI-TUMOR EFFECT OF ANTI-CANCER AGENT

(71) Applicants: Hirofumi Yamamoto, Suita-shi, Osaka (JP); Masaki Mori, Suita-shi, Osaka (JP)

(72) Inventors: Hirofumi Yamamoto, Suita (JP); Masaki Mori, Suita (JP); Yuichiro Doki, Suita (JP); Xin Wu, Suita (JP)

(73) Assignees: Hirofumi Yamamoto, Suita-shi, Osaka (JP); Masaki Mori, Suita-shi, Osaka (JP)

(*) Notice: Subject to any disclaimer, the term of this patent is extended or adjusted under 35 U.S.C. 154(b) by 0 days.

(21) Appl. No.: 15/119,862

(22) PCT Filed: Feb. 20, 2015

(86) PCT No.: PCT/JP2015/054843
§ 371 (c)(1),
(2) Date: Jan. 26, 2017

(87) PCT Pub. No.: WO2015/125934
PCT Pub. Date: Aug. 27, 2015

(65) Prior Publication Data
US 2017/0128487 A1    May 11, 2017

(30) Foreign Application Priority Data
Feb. 20, 2014 (JP) ................................ 2014-031060

(51) Int. Cl.
*A61K 33/06* (2006.01)
*A61K 31/513* (2006.01)
(Continued)

(52) U.S. Cl.
CPC ............ *A61K 33/06* (2013.01); *A61K 31/337* (2013.01); *A61K 31/513* (2013.01);
(Continued)

(58) Field of Classification Search
CPC ....................................................... A61K 33/06
See application file for complete search history.

(56) References Cited

U.S. PATENT DOCUMENTS

| | | | |
|---|---|---|---|
| 2008/0039521 | A1 | 2/2008 | Yasuda et al. |
| 2009/0137683 | A1 | 5/2009 | Yasuda et al. |
| 2014/0302145 | A1 | 10/2014 | Yamamoto et al. |

FOREIGN PATENT DOCUMENTS

| | | |
|---|---|---|
| JP | H06329557 A | 11/1994 |
| JP | 2009-242378 A | 10/2009 |

(Continued)

OTHER PUBLICATIONS

International Search Report in PCT/JP2015/054843, dated Apr. 14, 2015 (in 2 pages).
Fan, et al. 2013 "The reduction of tumor interstitial fluid pressure by liposomal imatinib and its effect on combination therapy with liposomal doxorubicin" *Biomaterials* 34: 2277-2288.

(Continued)

*Primary Examiner* — Benjamin Packard
(74) *Attorney, Agent, or Firm* — Knobbe, Martens, Olson & Bear, LLP (57) ABSTRACT

An object of the present invention is to provide an agent that potentiates the antitumor effect of an anticancer agent by allowing efficient accumulation of the anticancer agent in tumor tissue. The administration of carbonate apatite with the anticancer agent allows efficient accumulation of the anticancer agent in the tumor tissue to dramatically potentiate the antitumor effect of the anticancer agent.

7 Claims, 6 Drawing Sheets

(51) Int. Cl.
*A61K 33/24* (2006.01)
*A61K 31/555* (2006.01)
*A61K 31/337* (2006.01)
*A61K 31/704* (2006.01)

(52) U.S. Cl.
CPC .......... *A61K 31/555* (2013.01); *A61K 31/704* (2013.01); *A61K 33/24* (2013.01)

(56) References Cited

FOREIGN PATENT DOCUMENTS

| | | |
|---|---|---|
| JP | 2011-102255 A | 5/2011 |
| JP | 2011-144190 A | 7/2011 |
| JP | 5436650 B1 | 3/2014 |

OTHER PUBLICATIONS

Hossain, et al. 2013 "Fabrication and intracellular delivery of doxorubicin/carbonate apatite nanocomposites: Effect on growth retardation of established colon tumor" *PLOS ONE* 8(4): 1-11.

Hossanin, et al. 2007 "In vitro delivery of anti-cancer drugs to cancer cells by using inorganic nanoparticles" *The Japanese Society for Regenerative Medicine* 6: p. 312 (Abstract P-428).

Wu, et al. 2012 "Accumulation of pH-sensitive carbonate apatite nano-particles in subcutaneous human colon tumors" *Kai Proceedings of the Japanese Cancer Association*: No. 000173 (Abstract No. E-2010.

Wu X. et al. 2012 "Therapeutic doxorubicin-incorporating pH-sensitive carbonate apatite particles suppress tumor growth in a murine colon cancer model" *Kai The Japanese Association for Molecular Target therapy of Cancer* (Abstract No. W10-4) in 3 pages.

*HE stain*

GROUP ADMINISTERED 5-FU ALONE

GROUP ADMINISTERED 5-FU AND sCA PARTICLES

GROUP ADMINISTERED
DOXORUBICIN HYDROCHLORIDE
ALONE

GROUP ADMINISTERED
DOXORUBICIN HYDROCHLORIDE
AND sCA PARTICLES

ENHANCER OF ANTI-TUMOR EFFECT OF ANTI-CANCER AGENT

TECHNICAL FIELD

The present invention relates to a potentiating agent that potentiates the antitumor effect of an anticancer agent. The present invention also relates to a kit for treating cancer and an agent for treating cancer employing the potentiating agent.

BACKGROUND ART

Despite a recent upward trend in the survival rate of cancer patients along with the development of cancer therapeutic agents and methods, cancer still ranks first as a cause of death in Japan, and even today, more than 300,000 Japanese people die of cancer annually.

Cancer therapeutic methods are broadly classified into surgical therapy, radiotherapy, and chemotherapy. Among the above, chemotherapy involves administering an anticancer agent to a cancer patient. Chemotherapy is used before or after surgical therapy or radiotherapy, in preoperative or postoperative adjuvant chemotherapy for eradicating the lesion to enhance the healing power, or in the treatment of cancer that has spread throughout the body and cannot be treated with surgical therapy or radiotherapy. Conventionally, a variety of anticancer agents such as antimetabolites, alkylating agents, platinum agents, topoisomerase inhibitors, molecular target drugs, and antitumor antibiotics have been clinically put to practical use, and even expected to cure some cancers.

However, although the conventional anticancer agents have been found to produce certain therapeutic effects, they may not provide sufficient therapeutic effects, or may show variations in efficacy in some cases. Thus, the conventional anticancer agents in fact provide limited therapeutic effects through chemotherapy. Recently, therefore, in order to enhance the therapeutic effects provided through chemotherapy, various techniques for potentiating the antitumor effects of anticancer agents have been considered and proposed. Patent Literature 1, for example, reported that the antitumor effect of a platinum agent can be potentiated through the use of isosorbide dinitrate. Patent Literature 2 reported that the antitumor effect of an anticancer agent can be potentiated through the use of an aldo-keto reductase 1C family inhibitor. Patent Literature 3 reported that the antitumor effect of cisplatin can be potentiated through the use of phosphodiesterase IIIB inhibitor.

On the other hand, although anticancer agents enter tumor tissue to exhibit cytotoxicity, they may also act upon normal tissue simultaneously. If the anticancer agents act upon normal tissue, they cannot exhibit their original antitumor effects, and additionally, may induce various adverse effects. Thus, efficient accumulation of an anticancer agent in tumor tissue is expected to potentiate the antitumor effect, and will also be effective in reducing adverse effects. The techniques according to Patent Literatures 1 to 3, however, are not intended to potentiate the antitumor effects by efficiently accumulating the anticancer agents in tumor tissue. Drug delivery systems have also been conventionally developed in which drugs are contained in carriers such as liposomes for selective delivery of the drugs into tumors, which may enhance the ability of anticancer agents to accumulate in tumor tissue. The use of carriers used in such drug delivery systems, however, has a drawback in that the preparation of anticancer agents is complicated, and has difficulty in preventing accumulation of drugs in normal tissue such as liver, kidney, or the like.

Further, it is known that the interstitial fluid pressure in tumor tissue is higher than that in normal tissue. This high interstitial fluid pressure in tumor tissue is believed to be one major cause of the inability of a drug to penetrate deep into a tumor to exhibit a sufficient antitumor effect. Thus, in order to potentiate the antitumor effect of an anticancer agent, it would be effective to develop a drug that reduces the interstitial fluid pressure in tumor tissue, allows efficient accumulation of the anticancer agent in the tumor tissue, and allows penetration of the anticancer agent deep into the tumor tissue.

CITATION LIST

Patent Literature

Patent Literature 1: JP 2011-144190 A
Patent Literature 2: JP 2011-102255 A
Patent Literature 3: JP 2009-242378 A

SUMMARY OF INVENTION

Technical Problem

An object of the present invention is to provide an agent that potentiates the antitumor effect of an anticancer agent by allowing efficient accumulation of the anticancer agent in tumor tissue. Another object of the present invention is to provide a kit for treating cancer, which employs such a potentiating agent. Still another object of the present invention is to provide a drug that reduces the interstitial fluid pressure in tumor tissue.

Solution to Problem

As a result of extensive research to solve the aforementioned problem, the present inventors found that administration of carbonate apatite with an anticancer agent allows efficient accumulation of the anticancer agent in tumor tissue, which dramatically potentiates the antitumor effect of the anticancer agent. The inventors also found that carbonate apatite has the effect of reducing the interstitial fluid pressure in tumor tissue. Based on these findings, the inventors made further research to thereby accomplish the present invention.

Specifically, the present invention provides the following aspects.

Item 1. An agent for potentiating an antitumor effect of an anticancer agent, the agent containing carbonate apatite as an active ingredient.

Item 2. The agent according to item 1, wherein the carbonate apatite is in the form of nanoparticles with an average particle size of 50 nm or less.

Item 3. The agent according to item 1 or 2, wherein the anticancer agent is at least one selected from the group consisting of antimetabolites, platinum agents, microtubule inhibitors, and anticancer antibiotics.

Item 4. The agent according to any of items 1 to 3, wherein the anticancer agent is at least one selected from the group consisting of 5-fluorouracil, cisplatin, oxaliplatin, docetaxel, and doxorubicin hydrochloride.

Item 5. The agent according to any of items 1 to 4, further containing albumin.

Item 6. A kit for treating cancer including a first preparation containing an anticancer agent and a second preparation containing the agent according to any of items 1 to 5.

Item 7. An agent for treating cancer containing an anticancer agent and the agent according to any of items 1 to 5.

Item 8. An agent for reducing interstitial fluid pressure in tumor tissue, the agent containing carbonate apatite as an active ingredient.

Item 9. An agent for enhancing accumulation of a drug in tumor tissue, the agent containing carbonate apatite as an active ingredient.

Item 10. A method for treating cancer including the step of administering effective amounts of carbonate apatite and an anticancer agent to a cancer patient.

Item 11. A method for reducing interstitial fluid pressure in tumor tissue including the step of administering an effective amount of carbonate apatite to a cancer patient.

Item 12. A method for enhancing accumulation of a drug in tumor tissue including the step of administering effective amounts of carbonate apatite and a drug to a cancer patient.

Item 13. Use of carbonate apatite for production of an agent for potentiating an antitumor effect of an anticancer agent.

Item 14. Use of carbonate apatite for production of an agent for reducing interstitial fluid pressure in tumor tissue.

Item 15. Use of carbonate apatite for production of an agent for enhancing accumulation a drug in tumor tissue.

Advantageous Effects of Invention

In accordance with the present invention, an anticancer agent can be efficiently accumulated in tumor tissue, which allows the antitumor effect of the anticancer agent to be greatly potentiated. Hence, the present invention allows the anticancer agent to efficiently produce the antitumor effect against a tumor, which is expected to provide good news for cancer patients.

The effect of potentiating the antitumor effect of an anticancer agent in the present invention is believed to be produced based on the following mechanism of action. The interstitial fluid pressure in tumor tissue, which is higher than that in normal tissue, is considered as one major cause of preventing a drug from readily penetrating deep into a tumor. On the other hand, as described below in Example 7, carbonate apatite has been found to have the effect of reducing the interstitial fluid pressure in tumor tissue. The decrease in the interstitial fluid pressure in tumor tissue allows the anticancer agent to penetrate deep into the tumor tissue, which is believed to be a factor contributing to the potentiation of the antitumor effect of the anticancer agent. Of course, the present invention is not to be construed as being limited to this mechanism of action.

Further, by virtue of the effect of reducing the interstitial fluid pressure in tumor tissue described above, carbonate apatite also enhances accumulation of a drug other than anticancer agents (e.g., a drug used in photodynamic hyperthermal therapy or photodynamic therapy for cancer) in a tumor, and therefore, is also usable as an accumulation enhancer that enhances accumulation of the drug in the tumor tissue.

DESCRIPTION OF EMBODIMENTS

1. Potentiating Agent

The potentiating agent of the present invention is used for the purpose of potentiating the antitumor effect of an anticancer agent, and contains carbonate apatite as an active ingredient. Hereinafter, the potentiating agent of the present invention will be described in detail.

"Carbonate apatite" used in the present invention may have a known composition. Carbonate apatite may have a chemical structure in which the hydroxyl group (OH—) of hydroxy apatite ($Ca_{10}(PO_4)_6(OH)_2$) is partially replaced by a carbonic acid group ($CO_3^{2-}$), and such a chemical structure can be represented by the general formula: $Ca_{10-m}X_m(PO_4)_6(CO_3)_{1-n}Y_n$. In the formula, X may be an element capable of partially replacing Ca in the carbonate apatite, examples of which include Sr, Mn, and rare-earth elements. In the formula, m is generally a positive number not less than 0 and not more than 1, preferably not less than 0 and not more than 0.1, more preferably not less than 0 and not more than 0.01, and even more preferably not less than 0 and not more than 0.001. Y is a unit capable of partially replacing $CO_3$ in the carbonate apatite, examples which include OH, F, and Cl. In the formula, n is generally a positive number not less than 0 and not more than 0.1, preferably not less than 0 and not more than 0.01, more preferably not less than 0 and not more than 0.001, and even more preferably not less than 0 and not more than 0.0001.

Carbonate apatite used in the present invention is preferably in the form of nanoparticles with an average particle size of 50 nm or less, because it is administered to a living body to play the role of allowing an anticancer agent to accumulate in tumor tissue. The lower limit of the average particle size of the carbonate apatite nanoparticles is not limited as long as the desired effects set forth above can be obtained. For example, the average particle size of the carbonate apatite nanoparticles may have a lower limit of 1 nm or more, preferably 3 nm or more, and more preferably 5 nm or more. On the other hand, the upper limit of the average particle size of the carbonate apatite nanoparticles is more preferably 40 nm or less, even more preferably 30 nm or less, further more preferably 20 nm or less, and still more preferably 10 nm or less.

As described below in the Production Example, the average particle size of the carbonate apatite nanoparticles can be measured by observation using a scanning probe microscope. Before the measurement of the average particle size, the site to be measured should be observed with a CCD camera. As a result, when large particles clearly unsuitable for measurement with a scanning probe microscope are observed (for example, particles with diameters of 5 μm or more), such large particles will be excluded from the measurement. As used herein, the term "particle size" means the size of independent particles that can be individually identified when measured with a scanning probe microscope. Therefore, when a plurality of particles forms an aggregate, such an aggregate should be counted as a single particle.

While the potentiating agent of the present invention may be in any non-limiting form of preparation, it is preferably in the form of a dispersion, in view of efficiently potentiating the antitumor effect of the anticancer agent while suppressing reaggregation of the carbonate apatite particles to maintain the average particle size defined above.

The concentration of the carbonate apatite in the potentiating agent of the present invention is not limited, and may be appropriately set so as to provide the dose mentioned below, taking into account the method of administration or other factors. Where the potentiating agent of the present invention is a dispersion, for example, the concentration of the carbonate apatite may be from $1 \times 10^8$ to $1 \times 10^{12}$/ml, preferably from $1 \times 10^9$ to $1 \times 10^{11}$/ml, more preferably from $1 \times 10^{10}$ to $5 \times 10^{10}$/ml, even more preferably $3 \times 10^9$ to $3 \times 10^{10}$/ml, and further more preferably $6 \times 10^9$ to $1.5 \times 10^{10}$/ml.

Where the potentiating agent of the present invention is a dispersion, the solvent in which the carbonate apatite is dispersed is not limited as long as it is a pharmacologically acceptable solvent in which carbonate apatite can be dispersed. Specific examples of such solvents include a saline solution and other buffer solutions.

While the carbonate apatite with the average particle size described above may be produced in any non-limiting method, specifically, it may be produced, for example, by a method including the steps of preparing a dispersion in which carbonate apatite particles are dispersed in a pharmacologically acceptable solvent, and subjecting the dispersion to an ultrasonic vibration treatment.

The carbonate apatite particles can be obtained in accordance with a known method. For example, carbonate apatite particles containing a drug with antitumor activity can be produced by preparing an aqueous solution containing calcium ions, phosphate ions, and hydrogencarbonate ions, and incubating the solution. The concentration of each type of ions in the aqueous solution is not limited as long as carbonate apatite particles can be formed, and may be appropriately set with reference to the following.

The concentration of calcium ions in the aqueous solution may be generally 0.1 mM or more, preferably 0.5 mM or more, and more preferably 1 mM or more. The upper limit of the calcium ion concentration may be generally 1 M or less, preferably 100 mM or less, and more preferably 10 mM or less.

The concentration of phosphate ions in the aqueous solution may be generally 0.1 mM or more, preferably 0.5 mM or more, and more preferably 1 mM or more. The upper limit of the phosphate ion concentration may be generally 1 M or less, preferably 100 mM or less, and more preferably 10 mM or less.

The concentration of hydrogencarbonate ions in the aqueous solution may be generally 1.0 mM or more, preferably 5 mM or more, and more preferably 10 mM or more. The upper limit of the hydrogencarbonate ion concentration may be generally 10 M or less, preferably 1 M or less, and more preferably 100 mM or less.

Sources of calcium ions, phosphate ions, and hydrogencarbonate ions may each be of any non-limiting type capable of supplying the ions to the aqueous solution. For example, salts of these ions may be added as ion sources to the aqueous solution. More specifically, $CaCl_2$ may be used as a calcium ion source, $NaH_2PO_4 \cdot 2H_2O$ may be used as a phosphate ion source, and $NaHCO_3$ may be used as a carbonate ion source.

The respective ion sources may be mixed in any non-limiting order, and the aqueous solution may be prepared in any mixing order as long as the carbonate apatite particles can be obtained. For example, the aqueous solution can be prepared by a process including preparing a first solution containing calcium ions, separately preparing a second solution containing phosphate ions and hydrogencarbonate ions, and mixing the first and second solutions.

The aqueous solution for preparation of the carbonate apatite particles may contain components other than the respective ion sources described above in a range where the object is not impaired. For example, fluoride ions, chloride ions, Sr, Mn, or other species may be added to the aqueous solution so that in the composition, such a species can partially replace Ca or $CO_3$ in carbonate apatite. The added amount of fluoride ions, chloride ions, Sr, or Mn is preferably in a range where there is no significant effect on the pH-solubility of the formed complex particles or the particle size range of the formed complex particles. The aqueous solution for the preparation of the carbonate apatite particles may also be prepared using any of various cell culture media or buffers.

The carbonate apatite particles can be obtained by incubating, for a certain period of time, the aqueous solution containing each type of the ions described above, with the pH of the solution adjusted in the range of 6.0 to 9.0. In the process of forming the carbonate apatite particles, the pH of the aqueous solution is preferably 7.0 or more, more preferably 7.1 or more, even more preferably 7.2 or more, further more preferably 7.3 or more, still more preferably 7.4 or more, and most preferably 7.5 or more. On the other hand, in the process of forming the carbonate apatite particles, the pH of the aqueous solution is preferably 8.5 or less, and more preferably 8.0 or less.

In the process of forming the carbonate apatite particles, the temperature condition of the aqueous solution is generally 10° C. or higher, preferably 25° C. or higher, and more preferably 37° C. or higher. On the other hand, the upper limit of the temperature condition is generally 80° C. or lower, and preferably 70° C. or lower.

To form the carbonate apatite particles, the aqueous solution is generally incubated for a time period of 1 minute to 24 hours, and preferably 10 minutes to 1 hour. For example, whether or not the particles are formed can be checked by observation with a microscope.

In this way, a dispersion containing the carbonate apatite particles is formed. In the dispersion, the carbonate apatite particles have an average particle size of more than 50 nm. Thus, the carbonate apatite particles are subjected to a size-reducing treatment so that they can have an average particle size of 50 nm or less. Thus, the carbonate apatite particles with the above-defined average particle size can be obtained.

As described above, the carbonate apatite particles can be obtained from a solution of the respective ion source materials in a solvent such as water, a medium, or a buffer. The dispersion of the carbonate apatite particles obtained in this way is not always suitable for administration (intravascular administration) to a living body in terms of osmotic pressure, buffer capacity, sterility, or other properties. Therefore, the solvent in the dispersion of the carbonate apatite particles should be replaced by another solvent suitable for administration to a living body (such as a saline solution). For this purpose, it is generally necessary to perform a process including separating the carbonate apatite particles from the solvent by centrifugation, collecting the particles, and replacing the solvent by another solvent. If such a process is performed, however, the carbonate apatite particles can aggregate together to form large particles, so that the particles can rather change into a state unsuitable for administration to a living body. Thus, the dispersion medium in which the carbonate apatite particles have aggregated is replaced by a pharmacologically acceptable solvent suitable for administration to a living body, and then a size-reducing treatment is performed as described below, which makes it possible to obtain carbonate apatite nanoparticles with a desired average particle size dispersed in the pharmacologically acceptable solvent.

The method for size-reducing the carbonate apatite particles to an average particle size of 50 nm or less is preferably an ultrasonic vibration treatment. As used herein, the term "ultrasonic vibration treatment" does not refer to a treatment in which ultrasonic waves are applied to the specimen by bringing the specimen into direct contact with an ultrasonic vibrator of an ultrasonic crusher, a homogenizer, or other means for use in what is called cell-disruption or other procedures, but refers to a treatment using an ultrasonic cleaner having an ultrasonic vibrator and a cleaning tank integrated together generally for use in cleaning precision instruments, test tubes, or other objects. The ultrasonic vibration treatment means a process including placing a liquid (such as water) in the cleaning tank (water tank) of an ultrasonic cleaner, allowing a vessel (such as a plastic tube) to float in the liquid, wherein the vessel contains the dispersion in which the carbonate apatite particles are dispersed in the pharmacologically acceptable solvent, and applying ultrasonic waves to the dispersion through the liquid in a similar manner to cleaning precision instruments. This process makes it possible to conveniently and efficiently reduce the size of the carbonate apatite particles.

The ultrasonic vibration treatment may be performed using any non-limiting device capable of applying ultrasonic vibration indirectly to a vessel containing the carbonate apatite particles through a solvent such as water, like the above-described ultrasonic cleaner. In view of versatility and good handleability, an ultrasonic cleaner having an ultrasonic vibrator and a thermostatic tank is preferably used.

The ultrasonic vibration treatment may be performed under any non-limiting conditions as long as the average particle size can be controlled as desired. For example, the temperature of the water tank may be appropriately selected from temperatures ranging from 5 to 45° C., preferably from 10 to 35° C., and more preferably from 20 to 30° C. For example, the high-frequency power in the ultrasonic vibration treatment may be appropriately set in the range of 10 to 500 W, preferably 20 to 400 W, more preferably 30 to 300 W, and even more preferably 40 to 100 W. The oscillating frequency is generally from 10 to 60 Hz, preferably from 20 to 50 Hz, and more preferably from 30 to 40 Hz. For example, the time period of the ultrasonic vibration treatment may be appropriately set in the range of 30 seconds to 30 minutes, preferably 1 to 20 minutes, and more preferably 3 to 10 minutes.

In the process of performing the ultrasonic vibration treatment, any non-limiting type of vessel may be used to contain the dispersion containing the carbonate apatite particles as long as the average size of the carbonate apatite particles can be reduced in the desired range. Such a vessel may be appropriately selected depending on the volume of the dispersion or the intended use of the dispersion. For example, a plastic tube with a volume of 1 to 1,000 ml may be used.

The ultrasonic vibration treatment may be performed after albumin is added to the dispersion containing the carbonate apatite particles. This is because when the ultrasonic vibration treatment is performed in an environment where albumin and the carbonate apatite particles are present, carbonate apatite nanoparticles with a smaller size can be obtained, and reaggregation of particles can also be suppressed. The inclusion of albumin can also suppress reaggregation of the carbonate apatite nanoparticles having a reduced size. Where albumin is added to the dispersion containing the carbonate apatite particles, the amount of albumin added is not limited, but may be 0.1 to 500 mg/ml, for example, preferably 1 to 100 mg/ml, and more preferably 1 to 10 mg/ml, in view of making the carbonate apatite particles finer, and/or suppressing the reaggregation. Albumin thus added to make the carbonate apatite particles finer can be administered to a living body while being contained in the potentiating agent of the present invention together with the carbonate apatite particles.

The potentiating agent of the present invention is used for the purpose of potentiating the antitumor effect of an anticancer agent. While the anticancer agent whose antitumor effect is to be potentiated with the potentiating agent of the present invention may be of any non-limiting type, it is preferably an anticancer agent that can be incorporated into tumor cells to exhibit the antitumor effect. Examples of such anticancer agents include antimetabolites, platinum agents, alkylating agents, microtubule inhibitors, anticancer antibiotics, and topoisomerase inhibitors. Specific examples of antimetabolites include 5-fluorouracil, methotrexate, doxifluridine, tegafur, cytarabine, and gemcitabine. Specific examples of platinum agents include cisplatin, oxaliplatin, carboplatin, and nedaplatin. Specific examples of alkylating agents include cyclophosphamide, ifosfamide, thiotepa, carboquone, and nimustine hydrochloride. Specific examples of microtubule inhibitors include docetaxel, paclitaxel, vincristine, vindesine, and vinorelbine. Specific examples of anticancer antibiotics include doxorubicin hydrochloride, mitomycin, amrubicin hydrochloride, pirarubicin hydrochloride, epirubicin hydrochloride, aclarubicin hydrochloride, mitoxantrone hydrochloride, bleomycin hydrochloride, and peplomycin sulfate. Specific examples of topoisomerase inhibitors include irinotecan and nogitecan hydrochloride.

Antitumor effects of these anticancer agents can be potentiated with the potentiating agent of the present invention, either when they are used alone or in combination of two or more. Among these anticancer agents, antimetabolites, platinum agents, microtubule inhibitors, and anticancer antibiotics may be preferred, and 5-fluorouracil, cisplatin, oxaliplatin, docetaxel, and doxorubicin hydrochloride may be more preferred.

While the cancer to be treated with the potentiating agent of the present invention may be any non-limiting type as long as it is a cancer to which chemotherapy is applied, specific examples of such cancers include solid cancers such as colorectal cancer, colon cancer, gastric cancer, rectal cancer, liver cancer, pancreatic cancer, lung cancer, breast cancer, bladder cancer, prostatic cancer, cervical cancer, head and neck cancer, bile duct cancer, gallbladder cancer, and oral cancer; and blood cancers such as leukemia and malignant lymphoma. Among the above, solid cancers are suitable for treatment with the potentiating agent of the present invention.

The method of administration of the potentiating agent of the present invention is not limited, and may be either systemic or local administration. The potentiating agent of the present invention is remarkably advantageous in that even when administered systemically, the anticancer agent can be specifically accumulated in tumor tissue. Thus, systemic administration may be preferred, for example. Specifically, systemic administration may be intravascular (intraarterial or intravenous) administration, subcutaneous administration, subcutaneous administration, intraperitoneal administration, or the like, for example. Systemic administration is preferably intravascular administration, and more preferably intraarterial or intravenous administration. It will be understood that intravascular administration is intended to include not only intravascular injection but also continuous infusion. The method of administration of the potentiating agent of the present invention may be identical to or different from the method of administration of the anticancer agent whose antitumor effect is to be potentiated. Where the method of administration of the potentiating agent of the present invention is identical to that of the anticancer agent whose antitumor effect is to be potentiated, the anticancer agent and the potentiating agent of the present invention may be administered as a mixture, or may each be administered separately.

The dose of the potentiating agent of the present invention may be appropriately determined depending on the type of the anticancer agent whose antitumor effect is to be potentiated, the patient's sex, age, condition, and the like, and thus cannot be uniquely determined. For example, the potentiating agent of the present invention may be administered in a single dose containing about 10 mg to 1 g/kg (body weight) of carbonate apatite.

While the timing of administering the potentiating agent of the present invention is not limited, the potentiating agent may be administered concurrently with or within 24 hours before or after the administration of the anticancer agent whose antitumor effect is to be potentiated. The potentiating agent of the present invention is preferably administered concurrently with or within 12 hours before or after the administration of the anticancer agent, and more preferably, concurrently with or within 8 hours before or after the administration of the anticancer agent. In view of avoiding aggregation of the carbonate apatite nanoparticles before the administration of the potentiating agent of the present invention, it is preferable that the potentiating agent be administered quickly after the ultrasonic vibration treatment. For example, the potentiating agent of the present invention is preferably administered within 1 minute, preferably within 30 seconds, after the ultrasonic vibration treatment. However, when albumin is added to suppress the aggregation of the carbonate apatite nanoparticles as described above, the potentiating agent of the present invention can be administered several minutes to several tens of minutes after the ultrasonic vibration treatment.

2. Kit for Treating Cancer and Agent for Treating Cancer

The kit for treating cancer of the present invention, which is used to treat cancer by administering the potentiating agent using a method of administration identical to or different from that of an anticancer agent, includes a first preparation containing an anticancer agent and a second preparation containing the potentiating agent.

The agent for treating cancer of the present invention, which is used to treat cancer by administering the potentiating agent and anticancer agent in the same administration method, contains an anticancer agent and the potentiating agent in the same preparation (excluding a case where the anticancer agent is contained in the carbonate apatite).

The structures, modes of use, and the like of the kit for treating cancer and agent for treating cancer of the present invention are as described in the "1. Potentiating agent" section above.

3. Agent for Reducing Interstitial Fluid Pressure

Carbonate apatite has the effect of reducing the interstitial fluid pressure in tumor tissue, and therefore the present invention provides an agent for reducing interstitial fluid pressure utilizing carbonate apatite. Specifically, the agent for reducing interstitial fluid pressure of the present invention, which is used for the purpose of reducing the interstitial fluid pressure in tumor tissue, contains carbonate apatite as an active ingredient.

The composition, average particle size, method of production, method of administration, dose, target for application, and the like of the carbonate apatite used in the agent for reducing interstitial fluid pressure of the present invention are the same as those described in the "1. Potentiating agent" section above. The agent for reducing interstitial fluid pressure of the present invention can also reduce the interstitial fluid pressure in tumor tissue of a cancer patient to allow an anticancer agent, a diagnostic drug, a contrast agent, a drug used in photodynamic hyperthermal therapy or photodynamic therapy for cancer (e.g., indocyanine green or 5-aminolevulinic acid), or the like to be penetrated deep into the tumor.

4. Agent for Enhancing Accumulation

Carbonate apatite has the effect of enhancing the accumulation of various drugs in tumor tissue, and therefore the present invention provides an agent for enhancing accumulation utilizing carbonate apatite. Specifically, the agent for enhancing accumulation of the present invention, which is used for the purpose of enhancing accumulation of various drugs in tumor tissue, contains carbonate apatite as an active ingredient.

The composition, average particle size, method of production, method of administration, dose, target for application, and the like of the carbonate apatite used in the agent for enhancing accumulation of the present invention are the same as those described in the "1. Potentiating agent" section above. While the type of the drug to be accumulated in a tumor with the agent for enhancing accumulation of the present invention is not limited as long as it can attain a desired effect or purpose when accumulated in the tumor tissue, examples of the drug include an anticancer agent, a diagnostic drug, a contrast agent, and a drug used in photodynamic hyperthermal therapy or photodynamic therapy for cancer (e.g., indocyanine green or 5-aminolevulinic acid).

EXAMPLES

Hereinafter, the present invention will be described with reference to examples. It will be understood that the present invention is not to be construed as being limited to the following examples.

Production Example

Production of Carbonate Apatite Nanoparticles (Sonicated Carbonate Apatite; sCA)

(1) Production of carbonate apatite Nanoparticles (sCA) using DMEM solution

To 100 ml of distilled water, 1.35 g of DMEM powder and 0.37 g of $NaHCO_3$ were sequentially added and dissolved completely, and the pH of the solution was adjusted to 7.5 with 1N HCl. The DMEM solution (100 ml) was filtered through a 0.2 μm size filter, and 4 μl of $CaCl_2$ (1 M) was mixed per 1 ml of the DMEM solution. The resulting mixture was incubated in a water bath at 37° C. for 30 minutes. Subsequently, the mixture was centrifuged at 15,000 rpm for 5 minutes. The resulting pellet was dispersed in distilled water, a cell culture liquid, or an aqueous solution that can be administered to cells or a living body, such as a saline solution, so that a dispersion of carbonate apatite particles was obtained. The dispersion was subjected to an ultrasonic vibration treatment for 10 minutes, so that carbonate apatite nanoparticles (hereinafter referred to as "sCA (1) particles") were obtained. A plastic vessel containing the dispersion of carbonate apatite particles was allowed to float in water at 20° C. placed in a water bath having an ultrasonic vibration function, and the ultrasonic vibration treatment was performed under the conditions of a high-frequency power of 55 W and an oscillating frequency of 38 kHz for 10 minutes using the water bath. When the particle size was measured with a microscope, the sCA (1) particles were dispersed in distilled water after the centrifugation. When the dispersion was used for experiments with cells, the dispersion was prepared by dispersing the sCA (1) particles in the DMEM solution without or after the centrifugation. When the dispersion was used for experiments with animals, the dispersion was prepared by dispersing the sCA(1) particles in a saline solution after the centrifugation.

(2) Production of carbonate apatite Nanoparticles (sCA) using a Buffer

To 100 ml of distilled water, 0.37 g of $NaHCO_3$, 90 μl of $NaH_2PO_4 \cdot 2H_2O$ (1 M), and 180 μl of $CaCl_2$ (1 M) were sequentially added and dissolved, and the pH of the solution was adjusted to 7.5 with 1N HCl. The solution was filtered through a 0.2 μm size filter. The solution thus obtained will be hereinafter denoted as "buffer A". Four microliters of $CaCl_2$ (1 M) were mixed per 1 ml of buffer A, and the mixture was incubated in a water bath at 37° C. for 30 minutes. Subsequently, the mixture was centrifuged at 15,000 rpm for 5 minutes. The resulting pellet was dispersed in distilled water, a cell culture liquid, or an aqueous solution that can be administered to cells or a living body, such as a saline solution, so that a dispersion of carbonate apatite particles was obtained. The dispersion was subjected to an ultrasonic vibration treatment for 10 minutes, so that carbonate apatite nanoparticles (hereinafter referred to as "sCA (2) particles") were obtained. A plastic vessel containing the dispersion of carbonate apatite particles was allowed to float in water at 20° C. placed in a water bath having an ultrasonic vibration function, and the ultrasonic vibration treatment was performed under the conditions of a high-frequency power of 55 W and an oscillating frequency of 38 kHz for 10 minutes using the water bath. When the particle size was measured with a microscope, the sCA (1) particles were dispersed in distilled water after the centrifugation. When the dispersion was used for experiments with cells, the dispersion was prepared by dispersing the sCA(1) particles in the DMEM solution after the centrifugation. When the dispersion was used for experiments with animals, the dispersion was prepared by dispersing the sCA(1) particles in a saline solution after the centrifugation.

(3) Measurement of the Particle Size and Morphology of carbonate apatite Nanoparticles (sCA)

Figure 1:
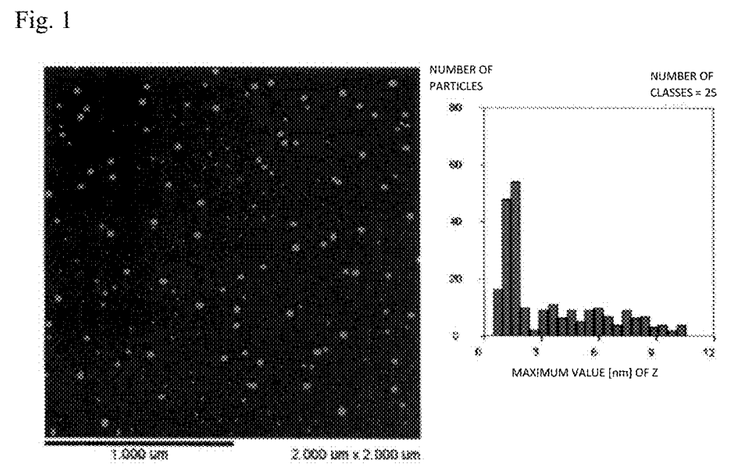
FIG. 1 shows the results of the measurement of the particle size and morphology of carbonate apatite nanoparticles (sCA (1) particles) obtained in the Production Example with a scanning probe microscope.
Figure 2:
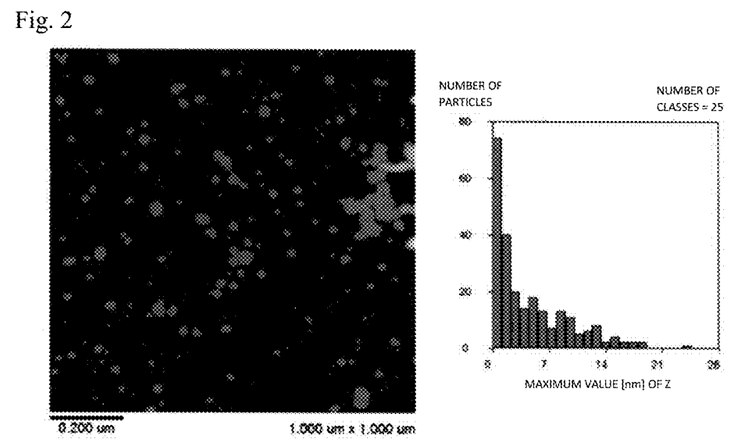
FIG. 2 shows the results of the measurement of the particle size and morphology of carbonate apatite nanoparticles (sCA (2) particles) obtained in the Production Example with a scanning probe microscope.

The particle size, morphology, and the like of the sCA(1) particles and sCA(2) particles prepared in Production Example 1 were measured using a scanning probe microscope (SPM-9500 manufactured by SHIMADZU CORPORATION) with a microcantilever (OMCL-AC240TS-RS manufactured by Olympus Corporation) in a dynamic mode. The measurement was performed twice within 30 seconds after the ultrasonic vibration treatment in each case. About 10 μl of the aqueous sample solution was dropped onto the surface of a cover glass. After the solution was vacuum-dried for 5 minutes, a smooth surface was selected with a CCD camera, and the particle size and morphology were measured within an area of 1 to 5 square μm. The results are shown in Table 1 below. FIGS. 1 and 2 each show a two-dimensional analysis image obtained for the measured area, as well as a graph illustrating a distribution of the number of particles according to size. FIG. 1 shows the sCA(1) particles, and FIG. 2 shows the sCA(2) particles. These results confirmed that the particle size of carbonate apatite particles can be reduced to 10 nm or less through the ultrasonic vibration treatment.

TABLE 1

| | sCA(1) particles | | sCA(2) particles | |
|---|---|---|---|---|
| | Measurement 1 | Measurement 2 | Measurement 1 | Measurement 2 |
| Average particle size (nm) | 2.649 | 3.502 | 4.564 | 3.269 |
| Measured area | 2 μm × 2 μm | | 1 μm × 1 μm | |
| Number of particles in the measured area | 307 | 235 | 242 | 283 |

Example 1

Potentiation of the Antitumor Effect of 5-fluorouracil

Human colorectal cancer cells (HCT116) were uniformly seeded on 96-well plates ($1 \times 10^4$ cells/well) and cultured overnight. The culture was performed under the conditions of 5% $CO_2$ and 37° C., using a DMEM medium supplemented with 10% fetal bovine serum. Next, the sCA(1) particles in an amount corresponding to the amount prepared from 38 μl of the DMEM solution in (1) of the Production Example above were dispersed in 100 μl of the cell culture liquid. The dispersion was added to each well, and the culture was performed under the conditions of 5% $CO_2$ and 37° C. for 24 hours. Subsequently, 5-fluorouracil was added in various concentrations, and the culture was performed under the conditions of 5% $CO_2$ and 37° C. At 24, 48, and 72 hours after the addition of 5-fluorouracil, the number of cells was counted, and $IC_{50}$ (concentration of 5-fluorouracil that kills 50% of the cancer cells) values were determined. For comparison, tests were performed under the same conditions except that the sCA particles were not added, and $IC_{50}$ values were determined.

The obtained results are shown in Table 2. These results show that in the presence of 5-fluorouracil and the carbonate apatite particles, the $IC_{50}$ values were reduced compared to those obtained using 5-fluorouracil alone. In particular, at 24 hours after the addition of 5-fluorouracil, the ICso value was significantly reduced in the presence of 5-fluorouracil and the carbonate apatite particles. These results revealed that the carbonate apatite particles potentiate the antitumor effect of 5-fluorouracil.

TABLE 2

| | $IC_{50}$ (mean ± SD) (μg/ml) | | |
|---|---|---|---|
| | After 24 hr | After 48 hr | After 72 hr |
| 5-fluorouracil alone | 215 ± 141 | 4.07 ± 0.473 | 2.64 ± 0.696 |
| 5-fluorouracil + sCA particles | 17.7 ± 2.56 | 1.67 ± 0.284 | 2.41 ± 0.142 |

Example 2

Potentiation of the Antitumor Effects of 5-Fluorouracil, Cisplatin, Oxaliplatin, and Docetaxel Human colorectal cancer cells (HCT116) were uniformly seeded on 24-well plates ($1\times10^4$ cells/well) and cultured overnight. The culture was performed under the conditions of 5% $CO_2$ and 37° C., using a DMEM medium supplemented with 10% fetal bovine serum. Next, the sCA(1) particles in an amount corresponding to the amount prepared from 1 ml of the DMEM solution in (1) of the Production Example above were dispersed in 2 ml of the cell culture liquid. The dispersion was added to each well, and the culture was performed under the conditions of 5% $CO_2$ and 37° C. for 24 hours. Subsequently, 5-fluorouracil, cisplatin, oxaliplatin, or docetaxel was added in various concentrations, and the culture was performed under the conditions of 5% $CO_2$ and 37° C. At 48 hours after the addition of each of the anticancer agents, the number of cells was counted, and the $IC_{50}$ (concentration of 5-fluorouracil that kills 50% of the cancer cells) value was determined. For comparison, tests were performed under the same conditions except that the sCA particles were not added, and $IC_{50}$ values were determined.

The obtained results are shown in Table 3. These results show that in the presence of the carbonate apatite particles with 5-fluorouracil, cisplatin, oxaliplatin, or docetaxel, the $IC_{50}$ value was reduced compared to that using each of these anticancer agents alone. In particular, the carbonate apatite particles significantly potentiated the antitumor effects of 5-fluorouracil, oxaliplatin, and docetaxel. That is, these results revealed that the carbonate apatite particles have the effect of potentiating the antitumor effects of the various anticancer agents.

TABLE 3

| | $IC_{50}$ (mean ± SD) | |
|---|---|---|
| | With sCA particles | Without sCA particles |
| 5-fluorouracil | 74.6 ± 10.0 μM | 11.7 ± 2.0 μM |
| Cisplatin | 39.2 ± 2.7 μM | 31.3 ± 0.9 μM |

TABLE 3-continued

| | $IC_{50}$ (mean ± SD) | |
|---|---|---|
| | With sCA particles | Without sCA particles |
| Oxaliplatin | 31.3 ± 2.2 μM | 3.70 ± 1.1 μM |
| Docetaxel | 9.17 ± 0.42 nM | 0.353 ± 0.07 nM |

Example 3

Potentiation of the Antitumor Effect of 5-fluorouracil Against Human Colon Cancer Cells A human colon cancer cell line (SW480) was uniformly seeded on 24-well plates ($1\times10^4$ cells/well) and cultured overnight. The culture was performed under the conditions of 5% $CO_2$ and 37° C., using a DMEM medium supplemented with 10% fetal bovine serum. Next, the sCA(1) particles in an amount corresponding to the amount prepared from 1 ml of the DMEM solution in (1) of the Production Example above were dispersed in 2 ml of the cell culture liquid. The dispersion was added to each well, and the culture was performed under the conditions of 5% $CO_2$ and 37° C. for 24 hours. Subsequently, 5-fluorouracil was added in 0.1, 0.25, 0.5, 1, 2, and 10 μg/ml, and the culture was performed under the conditions of 5% $CO_2$ and 37° C. for 72 hours. The number of viable cells after the culture was then counted. For comparison, tests were performed under the same conditions except that 5-fluorouracil or the sCA particles were not added, and the number of viable cells after the culture was counted. Each cell survival rate was calculated taking as 100% the number of viable cells after 72 hours of culture without the addition of 5-fluorouracil.

Figure 3:
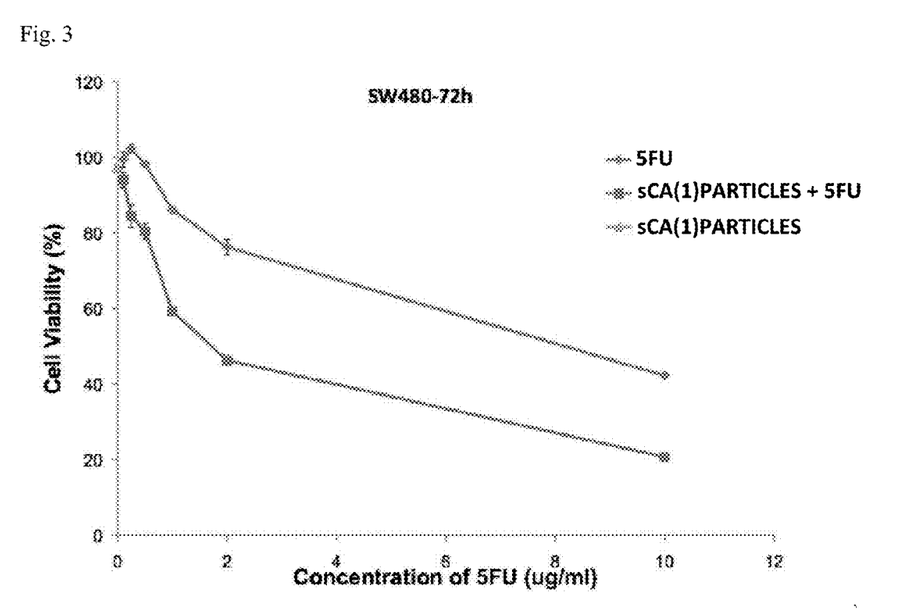
FIG. 3 shows the results of the measurement of an antitumor effect against a human colon cancer cell line (SW480) in the presence of 5-fluorouracil and the carbonate apatite particles in Example 3.

The obtained results are shown in FIG. 3. These results show that in the presence of 5-fluorouracil and the carbonate apatite particles, the cell survival rate was lower than that with 5-fluorouracil alone or the carbonate apatite particles alone, which confirmed that the carbonate apatite particles potentiated the antitumor effect of 5-fluorouracil.

Example 4

Potentiation of the Antitumor Effect of 5-fluorouracil Against Human Colorectal Cancer Cells Tests were performed as in Example 3, except that a human colorectal cancer cell line (DLD-1) was used instead of the human colon cancer cell line, and each cell survival rate was measured.

Figure 4:
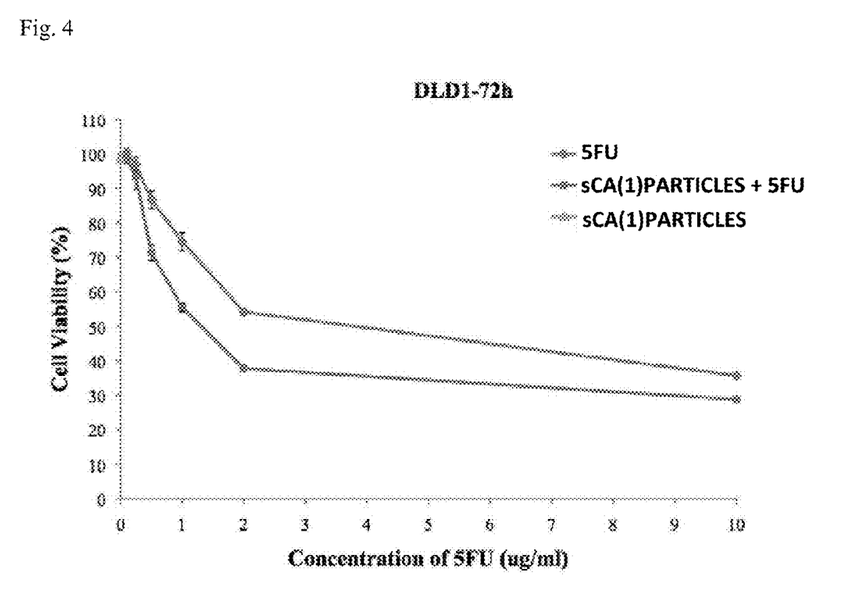
FIG. 4 shows the results of the measurement of an antitumor effect against a human colorectal cancer cell line (DLD-1) in the presence of 5-fluorouracil and the carbonate apatite particles in Example 4.

The obtained results are shown in FIG. 4. These results also confirmed that the carbonate apatite particles potentiate the antitumor effect of 5-fluorouracil, as in Example 3.

Example 5

Potentiation of the Antitumor Effect of doxorubicin hydrochloride Against Human Colorectal Cancer Cells A human colorectal cancer cell line (HCT116) was uniformly seeded on 24-well plates ($1\times10^4$ cells/well) and cultured overnight. The culture was performed under the conditions of 5% $CO_2$ and 37° C., using a DMEM medium supplemented with 10% fetal bovine serum. Next, sCA(0.5)

was obtained by dispersing the sCA(1) particles in an amount corresponding to the amount prepared from 1 ml of the DMEM solution in (1) of the Production Example above in 2 ml of the cell culture liquid; sCA(1.0) was obtained by dispersing the sCA(1) particles in an amount corresponding to the amount prepared from 1 ml of the DMEM solution in (1) of the Production Example above in 1 ml of the cell culture liquid; and sCA(2.0) was obtained by dispersing the sCA(1) particles in an amount corresponding to the amount prepared from 1 ml of the DMEM solution in (1) of the Production Example above in 0.5 ml of the cell culture liquid. To each well was added 250 μl of each of these dispersions, and the culture was performed under the conditions of 5% $CO_2$ and 37° C. for 24 hours. Subsequently, 250 μl of a 1000 nmol/l solution of doxorubicin hydrochloride was added, and the culture was performed under the conditions of 5% $CO_2$ and 37° C. for 24 hours. Next, the cultured cells were collected, and fluorescence emitted by doxorubicin hydrochloride was measured by FACS. For comparison, tests were performed under the same conditions except that the sCA(1) particles were not added.

Figure 5:
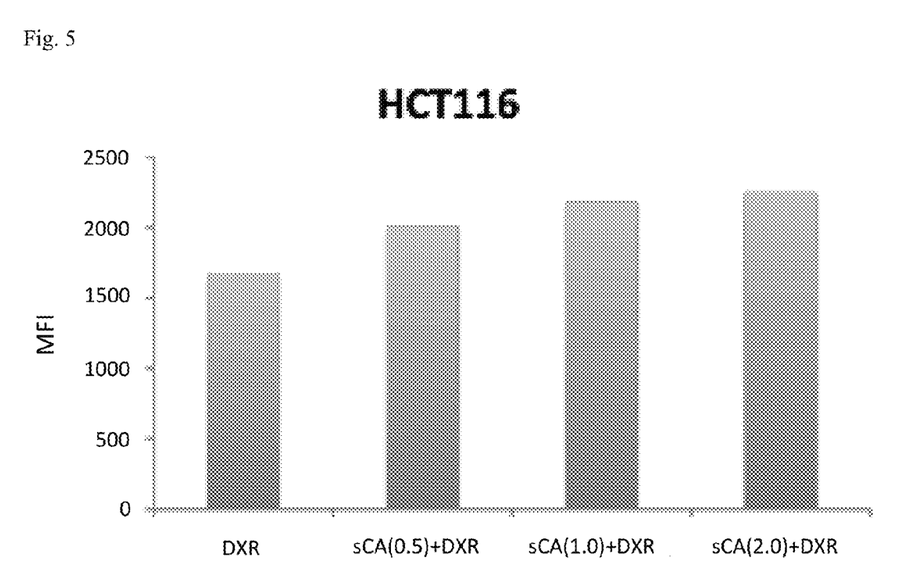
FIG. 5 shows the results of the measurement of an antitumor effect against a human colorectal cancer cell line (HCT116) in the presence of doxorubicin hydrochloride and the carbonate apatite particles in Example 5.

The obtained results are shown in FIG. 5. These results show that in the presence of doxorubicin hydrochloride and the carbonate apatite particles, the amount of doxorubicin hydrochloride incorporated into the cells increased compared to that with doxorubicin hydrochloride alone, which revealed that the uptake of doxorubicin hydrochloride into the cells was enhanced by the carbonate apatite particles.

Example 6

Potentiation of an Antitumor Effect in Tumor Model Mice (1)

The human colorectal cancer cell line HCT116 was subcutaneously injected into the left and right backs of 7 week-old BALB/cA nude mice (produced by CLEA Japan, Inc.) to produce solid tumor-bearing model mice. At the time when the tumor size reached 5 to 6 mm, the mice were randomly divided into the two groups: a group administered 5-FU alone and a group administered 5-FU and the sCA particles. Taking the time when the tumor size reached 5 to 6 mm as day 0, the drug was administered in the modes shown in Table 4 on day 0, 2, 7, 8, 9, and 10. On day 15, tumors were removed from the mice, and stained with hematoxylin-eosin (HE staining).

TABLE 4

| Group | Mode of administration |
|---|---|
| Group administered 5-FU alone | 5-fluorouracil was intraperitoneally administered in a dose of 30 mg/kg (body weight). |
| Group administered 5-FU and the sCA particles | 5-fluorouracil was intraperitoneally administered in a dose of 30 mg/kg (body weight), and 200 μl of a saline solution containing the sCA(2) particles in an amount corresponding to the amount prepared from 50 ml of buffer A in (2) of the Production Example above was administered via the tail vein. |

Figure 6:
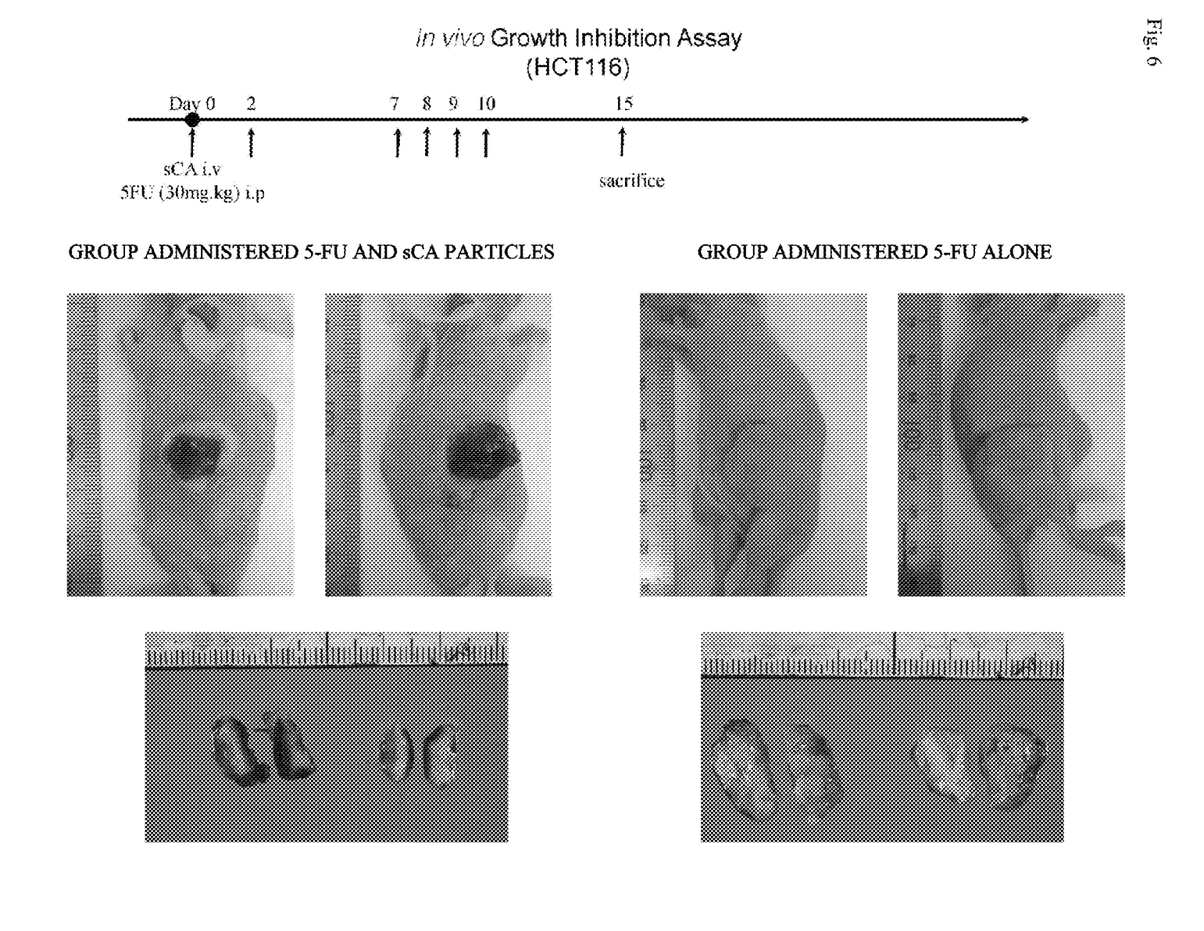
FIG. 6 shows the results of observation of the tumor size after the administration of 5-fluorouracil and the carbonate apatite particles to tumor model mice in Example 6.
Figure 7:
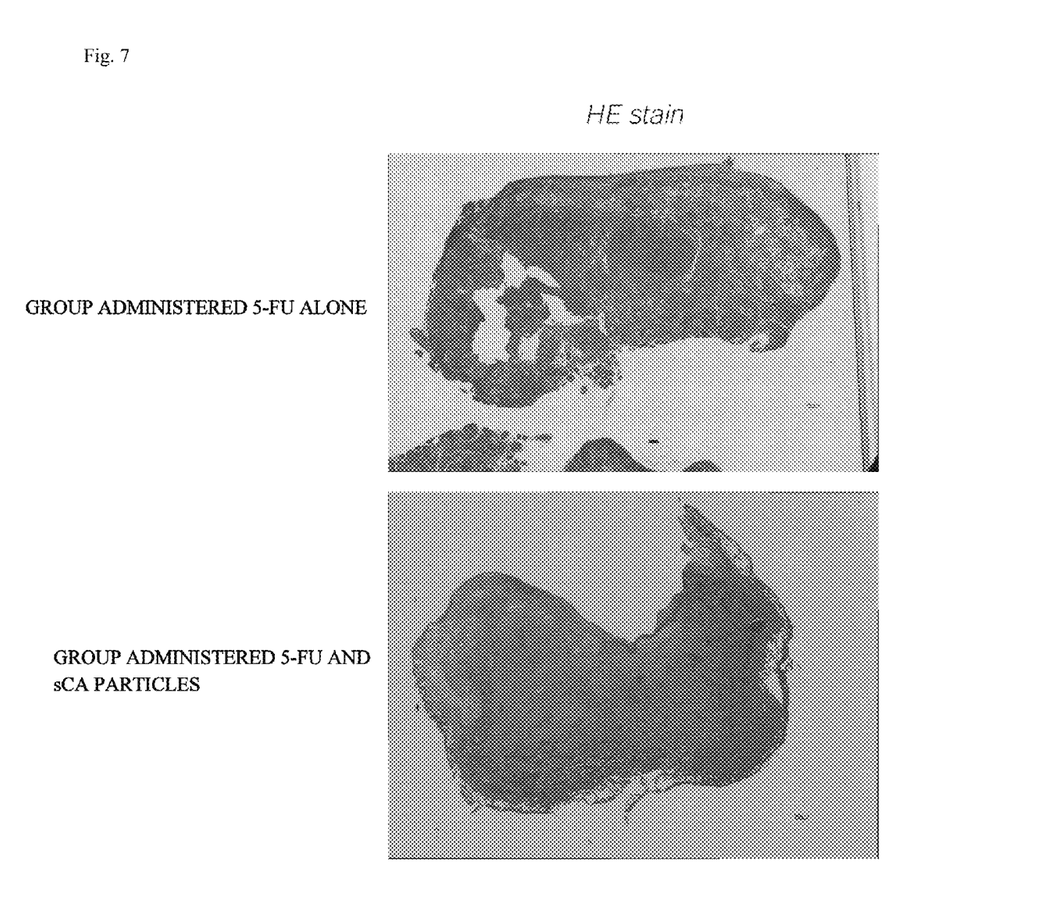
FIG. 7 shows the results of HE staining of tumor tissue removed after the administration of 5-fluorouracil and the carbonate apatite particles to tumor model mice in Example 6.

The obtained results are shown in FIGS. 6 and 7. These results show that when both 5-fluorouracil and the carbonate apatite particles were administered, the tumor size was smaller (FIG. 6) and the number of cancer cells killed in the tumor tissue was greater (FIG. 7) than those when 5-fluorouracil was administered alone.

Example 7

Potentiation of an Antitumor Effect in Tumor Model Mice (2)

Figure 8:
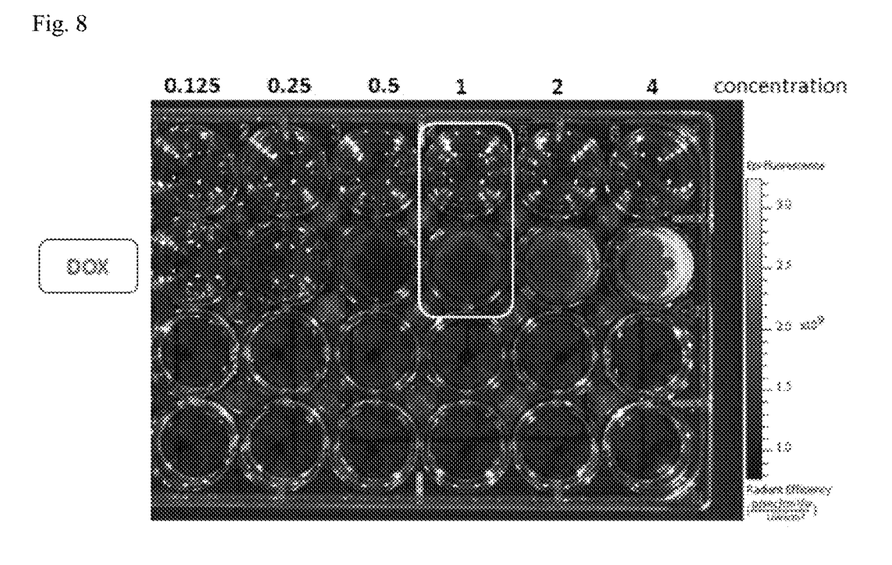
FIG. 8 is a diagram showing that fluorescence wavelength is detected by the IVIS Spectrum for doxorubicin (DOX).

The human colorectal cancer cell line HT29 ($5\times10^6$ cells) was subcutaneously injected into the left and right backs of 7 week-old BALB/cA nude mice (produced by CLEA Japan, Inc.) to produce murine subcutaneous solid tumor models. At the time when the tumors reached about 10 mm in diameter, the mice were randomly divided into the two groups shown in Table 5, and each group was administered the drug. After 2 hours from the drug administration, tumors were removed from the mice, and doxorubicin hydrochloride accumulated in the tumors was detected by fluorescent imaging using the IVIS Spectrum. For doxorubicin (DOX), detection of fluorescence wavelength has been confirmed by the IVIS Spectrum (FIG. 8).

TABLE 5

| Group | Mode of Administration |
|---|---|
| Group administered doxorubicin hydrochloride alone | Doxorubicin hydrochloride was administered via the tail vein in a dose of 1.5 mg/mouse |
| Group administered doxorubicin hydrochloride and the sCA particles | Doxorubicin hydrochloride was administered via the tail vein in a dose of 1.5 mg/mouse, and 200 μl of a saline solution containing the sCA(2) particles in an amount corresponding to the amount prepared from buffer A in (2) of the Production Example above was administered via the tail vein (3 hours prior to the administration of doxorubicin hydrochloride). |

Figure 9:
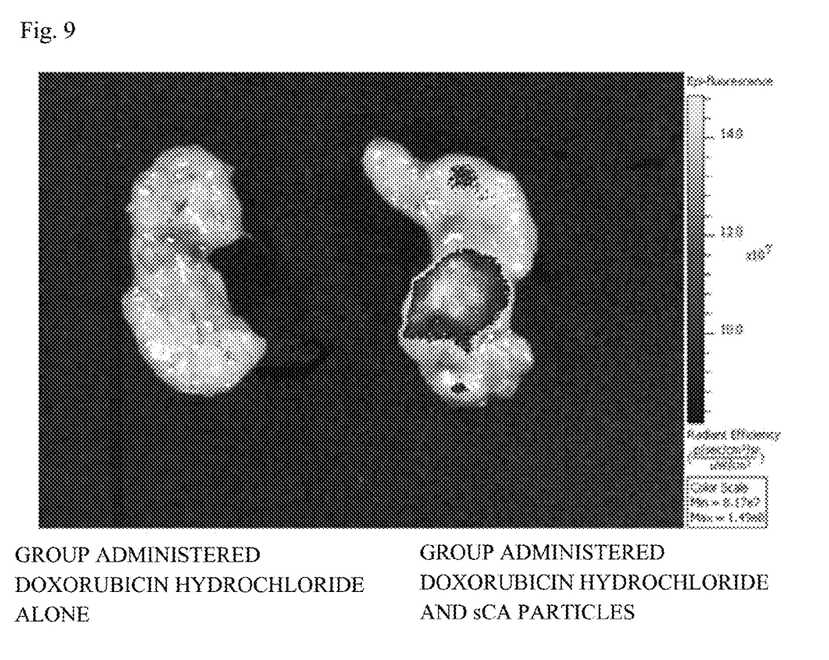
FIG. 9 shows the results of detection of doxorubicin by the IVIS Spectrum in tumor tissue removed after 2 hours from the administration of doxorubicin hydrochloride and the carbonate apatite particles to tumor model mice in Example 7.

The obtained results are shown in FIG. 9. As shown in FIG. 9, in the group administered doxorubicin hydrochloride alone, only a small amount of doxorubicin was detected in the tumor; on the contrary, in the group administered doxorubicin hydrochloride and the sCA particles, doxorubicin was found to be accumulated in the tumor. That is, these results revealed that the sCA particles allow doxorubicin hydrochloride to be efficiently accumulated in tumors in a short period of time, i.e., even in 2 hours after the administration.

Example 8

Decrease in the Interstitial Fluid Pressure in Tumor Tissue

The human colorectal cancer cell line HT29 ($5\times10^6$ cells) was subcutaneously injected into the left and right backs of 7 week-old BALB/cA nude mice (produced by CLEA Japan, Inc.) to produce murine subcutaneous solid tumor models. At the time when the tumors reached about 10 mm in diameter, 200 μl of a saline solution containing the sCA(2) particles prepared above (in an amount corresponding to the amount prepared from 50 ml of buffer A in (2) of the Production Example above) was administered via the tail vein. After 2.5 to 4 hours from the administration of the sCA(2) particles, the interstitial fluid pressure in each tumor was measured (the number of tumors for measurement: 3; n=39) using an in vivo pressure catheter measurement system (transonic science, Inc) equipped with a 1.6 Fr pressure catheter. As a control, the interstitial fluid pressure in each tumor prior to the administration of the sCA(2) particles was measured (the number of tumors for measurement: 5; n=30).

The obtained results are shown in Table 6. These results revealed that the carbonate apatite particles have the effect of reducing the interstitial fluid pressure in the tumor. These results suggest that the effect of reducing the interstitial fluid pressure in the tumor attained by the carbonate apatite particles contributes to the potentiation of the antitumor effect observed in the murine subcutaneous solid tumor models in Examples 6 and 7 above.

TABLE 6

|  | Average value (mmHg) of the interstitial fluid pressure in tumor | Standard deviation | Average standard error |
|---|---|---|---|
| Prior to the administration of the sCA(2) particles (n = 30) | 30.92 | 15.72 | 2.87 |
| After 2.5 to 4 hours from the administration of the sCA(2) particles (n = 39) | 13.40 | 11.49 | 1.84 |

The invention claimed is:

1. A method for treating cancer comprising the step of administering effective amounts of carbonate apatite particles and an anticancer agent to a cancer patient, wherein the anticancer agent is not contained in the carbonate apatite particles and wherein the carbonate apatite particles reduce interstitial fluid pressure in a tumor tissue in the cancer patient.

2. The method according to claim 1, wherein the carbonate apatite is in the form of nanoparticles with an average particle size of 50 nm or less.

3. The method according to claim 1, wherein the anticancer agent is at least one selected from the group consisting of antimetabolites, platinum agents, microtubule inhibitors, and anticancer antibiotics.

4. The method according to claim 1, wherein the anticancer agent is at least one selected from the group consisting of 5-fluorouracil, cisplatin, oxaliplatin, docetaxel, and doxorubicin hydrochloride.

5. The method according to claim 1, further comprising albumin.

6. A method for reducing interstitial fluid pressure in tumor tissue comprising the step of administering an effective amount of carbonate apatite particles to a cancer patient, wherein an anticancer agent is not contained in the carbonate apatite particles and wherein the carbonate apatite particles reduce interstitial fluid pressure in a tumor tissue in the cancer patient.

7. A method for enhancing accumulation of a drug in tumor tissue comprising the step of administering effective amounts of carbonate apatite and a drug to a cancer patient, wherein the drug is not contained in the carbonate apatite particles and wherein the carbonate apatite particles reduce interstitial fluid pressure in a tumor tissue in the cancer patient.

* * * * *